(12) United States Patent  
Schon et al.

(10) Patent No.: US 7,850,666 B2
(45) Date of Patent: Dec. 14, 2010

(54) CATHETER INFUSION PORT

(75) Inventors: Donald A Schon, Paradise Valley, AZ (US); Timothy M Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 362 days.

(21) Appl. No.: 11/335,369

(22) Filed: Jan. 19, 2006

(65) Prior Publication Data
US 2006/0184142 A1    Aug. 17, 2006

Related U.S. Application Data

(60) Provisional application No. 60/645,678, filed on Jan. 21, 2005.

(51) Int. Cl.
*A61M 37/00* (2006.01)
(52) U.S. Cl. .............. 604/288.02; 604/288.01; 604/288.04
(58) Field of Classification Search ........ 604/175, 604/288.01, 288.02, 288.03, 288.04
See application file for complete search history.

(56) References Cited

U.S. PATENT DOCUMENTS

| | | |
|---|---|---|
| 4,673,394 A | 6/1987 | Fenton, Jr. et al. |
| 4,692,146 A | 9/1987 | Hilger |
| 4,704,103 A | 11/1987 | Stober et al. |
| 4,767,410 A | 8/1988 | Moden et al. |
| 4,929,236 A | 5/1990 | Sampson et al. |
| 5,041,098 A | 8/1991 | Loiterman et al. |
| 5,045,060 A | 9/1991 | Melsky et al. |
| 5,108,377 A | 4/1992 | Cone et al. |
| 5,167,638 A | 12/1992 | Felix et al. |
| 5,360,407 A | 11/1994 | Leonard et al. |
| 5,387,192 A | 2/1995 | Glantz et al. |
| 5,399,168 A | 3/1995 | Wadsworth, Jr. et al. |
| 5,562,617 A | 10/1996 | Finch, Jr. et al. |
| 5,562,618 A | 10/1996 | Cai et al. |
| 5,688,237 A | 11/1997 | Rozga et al. |
| 5,718,682 A | 2/1998 | Tucker |
| 5,755,780 A | 5/1998 | Finch, Jr. et al. |
| 5,792,104 A | 8/1998 | Speckman et al. |
| 5,951,512 A | 9/1999 | Dalton |

(Continued)

OTHER PUBLICATIONS

International Preliminary Report on Patentability, PCT/US06/002057, dated Sep. 7, 2007 (5 pages).

*Primary Examiner*—Nicholas D Lucchesi
*Assistant Examiner*—Victoria P Campbell
(74) *Attorney, Agent, or Firm*—Blank Rome LLP

(57) ABSTRACT

A port (100) for a catheter assembly (200), including a body (102) and a cover (150) and having a distal discharge port (116) for connection to an implanted catheter assembly. Within the body is a longitudinal U-shaped channel (120) extending to a proximal body wall (104) from the distal body wall (106) along a longitudinal axis parallel to the axis of the discharge port (116). The channel has a rounded bottom (122) and is also rounded at the channel ends (126,124) at the distal and proximal body walls. The cover (150) provides for penetration by a syringe needle and seals upon needle withdrawal, with the cover having an inside surface (152) concave and rounded between the distal and proximal ends and also longitudinally, being generally smoothed into the channel sides and ends. The port has no inner sharp edges or corners and eliminates blood clotting and unwanted growth sites.

13 Claims, 3 Drawing Sheets

U.S. PATENT DOCUMENTS

| | | |
|---|---|---|
| 6,039,712 A | 3/2000 | Fogarty et al. |
| 6,086,555 A | 7/2000 | Eliasen et al. |
| 6,190,352 B1 | 2/2001 | Haarala et al. |
| 6,213,973 B1 | 4/2001 | Eliasen et al. |
| 6,471,689 B1 | 10/2002 | Joseph et al. |
| 6,527,754 B1 | 3/2003 | Tallarida et al. |
| 6,562,023 B1 | 5/2003 | Marrs et al. |
| 6,878,137 B2 | 4/2005 | Benchetrit |
| 7,513,892 B1 * | 4/2009 | Haarala et al. ......... 604/288.02 |
| 2004/0064110 A1 | 4/2004 | Forsell |
| 2004/0204692 A1 | 10/2004 | Eliasen |
| 2004/0254537 A1 | 12/2004 | Conlon et al. |

* cited by examiner

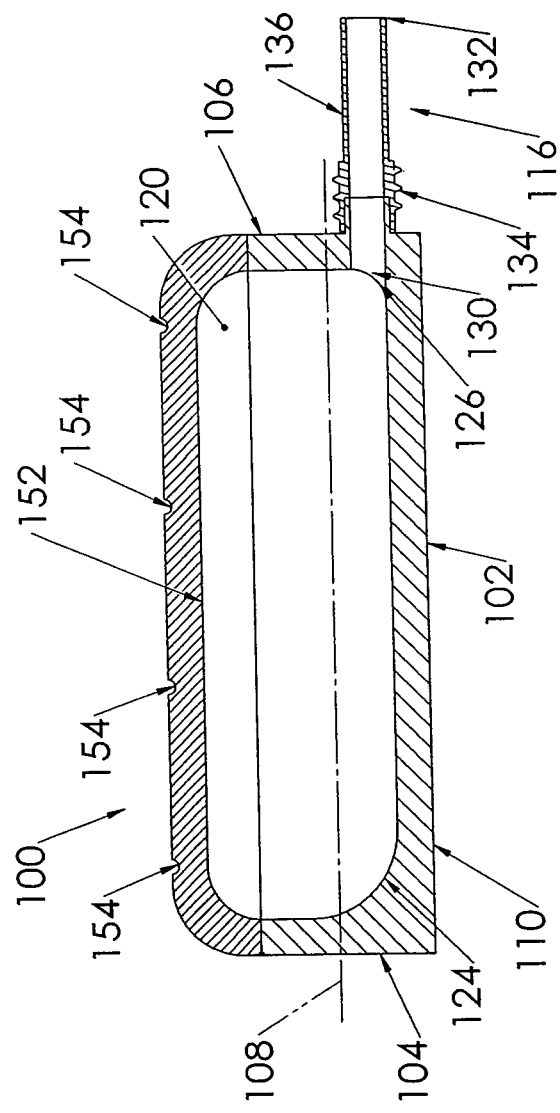
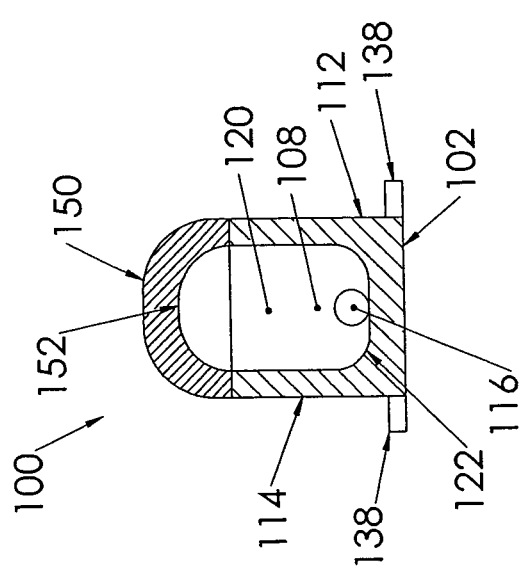

CATHETER INFUSION PORT

CROSS-REFERENCE TO RELATED APPLICATION

This application claims priority from U.S. Provisional Patent Application Ser. No. 60/645,678 filed Jan. 21, 2005.

FIELD OF THE INVENTION

The present invention relates to a port for injecting a fluid into or for withdrawing a fluid from a catheter.

BACKGROUND OF THE INVENTION

Infusion ports for the infusion and/or withdrawal of fluids from a patient are well-known. These ports are typically used for drug infusion or small amounts of blood withdrawal, where large flows of fluid are not required. However, larger ports are used for activities such as hemodialysis or plasmapheresis. Typically, these ports incorporate mechanical valves which open during use, such as when a needle is inserted into the port, and which close in between use, such as when the needle is removed from the port.

Such ports may be implanted subcutaneously and remain within the patient for prolonged periods of time. The ports provide an access site for multiple needle sticks without the need to continuously search for new access sites. However, many of the present port designs include interior portions having sharp edges and/or corners, which provide ideal locations for blood within the port to clot, or to provide a suitable location for bacterial or fungal growth. Additionally, for the port designs that include valves, the moving parts associated with the valves may malfunction or wear over time, necessitating the removal of the port.

It would be beneficial to provide a port that eliminates blood clotting and unwanted growths. Additionally, it would be beneficial to be able to remove and replace the port without undue difficulty.

SUMMARY OF THE INVENTION

The present invention is a port for a catheter assembly, having a generally elongated body having a discharge port that extends through a distal wall, and a channel extending along the longitudinal axis to the proximal wall. The channel is U-shaped with a rounded portion disposed adjacent the bottom of the body and further having rounded corners adjacent the proximal and distal walls of the body. A cover for the body provides for insertion therethrough of a syringe needle for infusion and that seals upon needle withdrawal; the cover includes an inside surface that is convex upwardly and is rounded at its sides and ends to be generally smoothed into the sidewalls of the channel and the proximal and distal end walls of the body. Thus, the port is devoid of any sharp edges or corners, therefore eliminating an avenue of blood clotting and unwanted growths.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 2 is a lateral sectional view of the catheter port taken along lines 2-2 of FIG. 1;

FIG. 3 is a longitudinal sectional view of the port shown in FIG. 1.

DETAILED DESCRIPTION OF THE INVENTION

Figure 1:
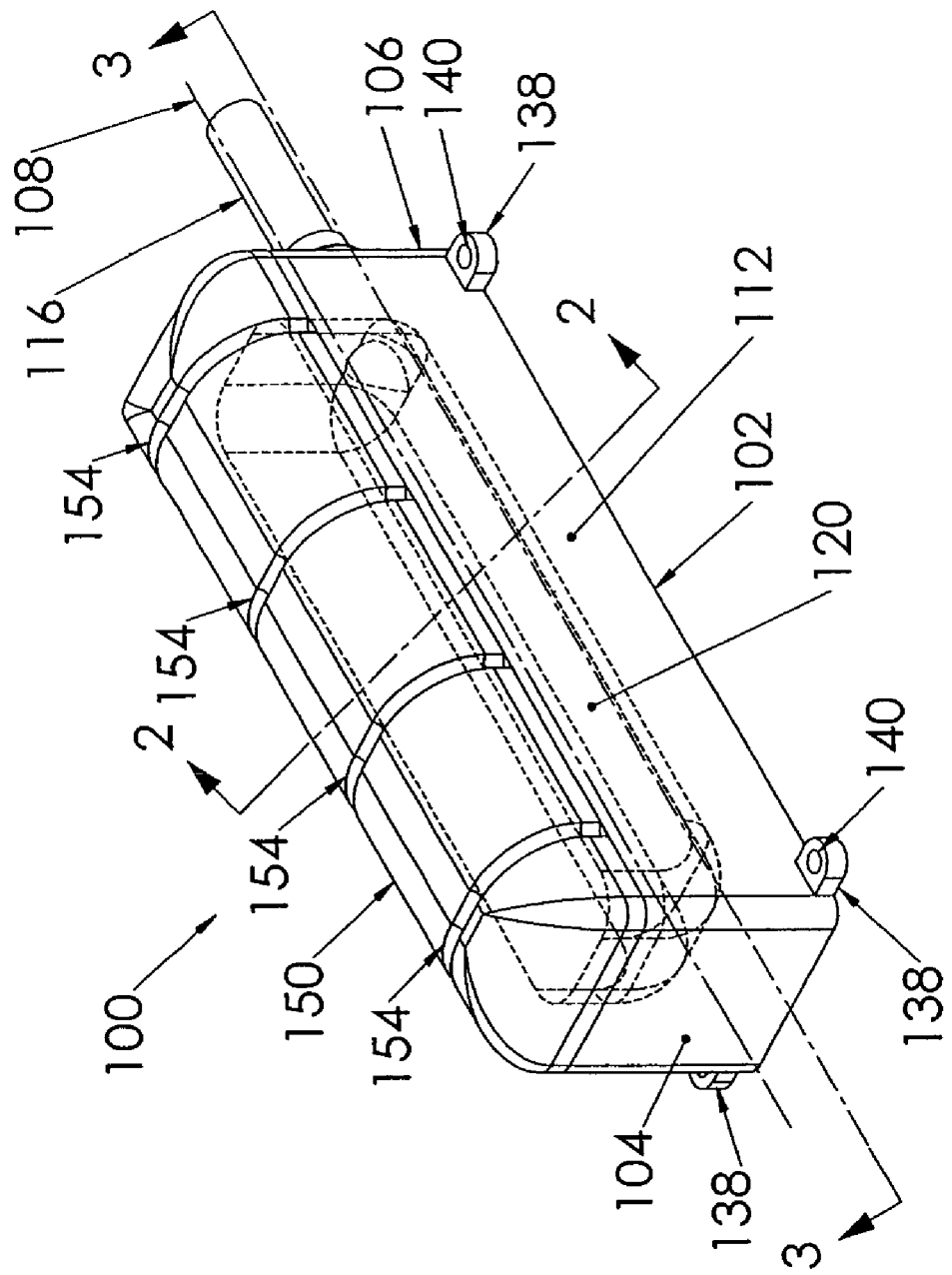
FIG. 1 is a perspective view of the catheter port according to a first embodiment of the present invention.

In the drawings, like numerals indicate like elements throughout. As used herein, the terms "distal" and "proximal" are defined to mean directions closer to and away from, respectively, a catheter connection port of the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

A catheter port 100 according to a preferred embodiment of the present invention is shown in FIG. 1. The port 100 is used to provide a connection to a catheter that has previously been subcutaneously implanted into a patient, such as to administer medicaments or other fluids, or to withdraw fluids, such as blood, from the patient. For example, the port 100 may be used for hemodialysis, apheresis, or, in a smaller embodiment, for the administration of medication.

The port 100 includes a generally elongated body 102 having a proximal end wall 104, a distal end wall 106, and a longitudinal axis 108 that extends longitudinally therethrough between the proximal and distal end walls and having a bottom wall 110 and side walls 112,114. Preferably, the body 102 is constructed from a biocompatible material, such as titanium, stainless steel, or some other suitable material, where the material is sufficiently hard to prevent needle penetration through a side or end wall or the bottom wall. Preferably, the body 102 is of a constant narrow width. Further, preferably, the body 102 is approximately 5 cm long, 3 cm high, and 2.5 cm wide, although those skilled in the art will recognize that the body 102 may be other dimensions as well.

A discharge port 116 extends through the distal wall 106 distal of the body 102. A generally elongated channel 120 extends along the longitudinal axis 108 between the proximal end wall 104 and the distal wall 106. A cross section of the port 100 showing the channel 120 is shown in FIG. 2. As seen in FIG. 2, the channel 120 is generally U-shaped in cross section, with a rounded portion 122 of the channel 120 disposed along the bottom wall 110 of the body 102, and with rounded channel ends 126,124 along the proximal and distal end walls 104,106 of the body 102. It is important that there are no hard edges or corners in the channel 120 because such corners or hard edges would allow blood to gather and coagulate, which may lead to malfunction of the port, or may lead to the growth of bacterial or fungal organisms, which are to be avoided.

The discharge port 116 includes a proximal end 130 that ends at the channel 120 and a distal end 132 that ends exterior of the body 102. The proximal end 130 connects to the channel 120 with a rounded or beveled taper, eliminating any sharp edges or corners. Distal end 132 is in fluid communication with the channel 120 and includes a threaded connector 134 adapted to threadably connect to a catheter. The distal end 132 of the discharge port 116 includes a lumen 136 that is inserted into the catheter.

As shown in FIGS. 1 and 2, a plurality of suture wings 38 extend from the body 102 generally away from the longitudinal axis 108. Preferably, the wings 138 extend in a plane co-planar with the bottom of the body 102, as shown in FIG. 2. The wings 138 are generally semi-circular with a suture hole 140 disposed therein to allow a suture to pass through to secure each suture wing 138 to the patient's skin.

A cover 150 is disposed over the body 102 to cover the channel 120 and to form the channel 120 into a closed volume. As shown in FIG. 2, the cover 150 may be generally convex in shape, with each end of the cover 150 curving into each respective proximal wall 104 and distal wall 106. It is important that there are no hard edges or corners along the inside surface 152 of the cover 150; instead, the inside surface 152 is rounded at the sides and ends adjoining the body 102 and generally smoothed into the side and end surfaces of channel 120. The cover 150 is preferably connected to the body 102 with an adhesive.

Figure 4:
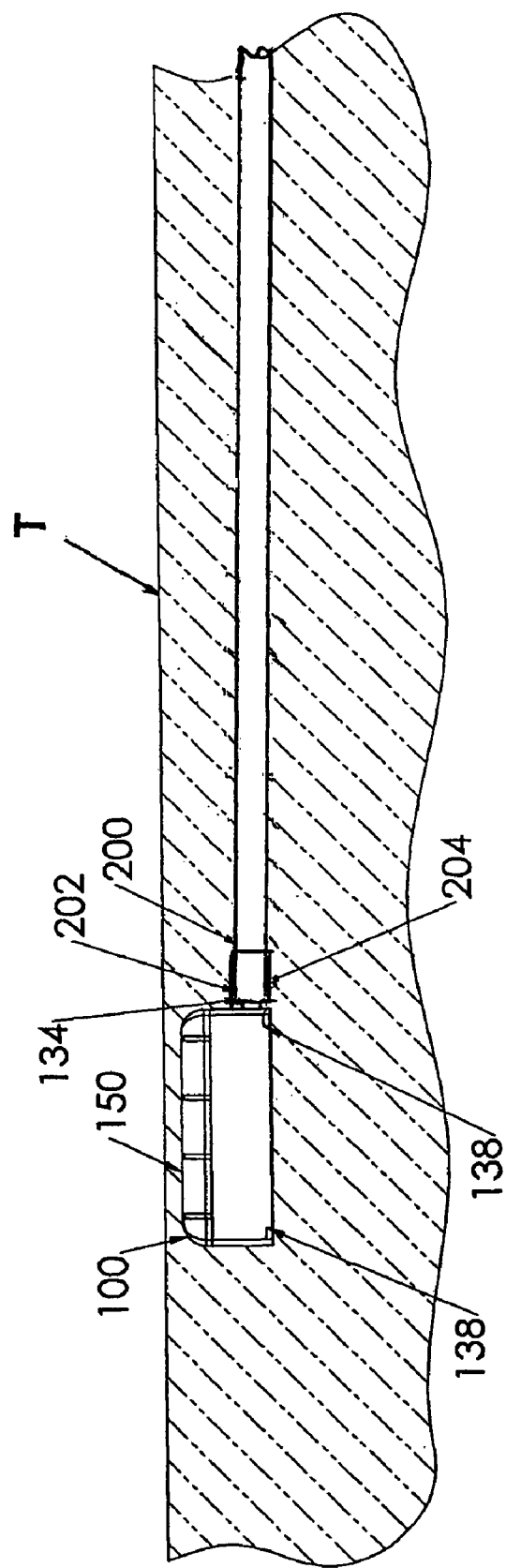
FIG. 4 is a side profile view, partially in section, of the catheter port of FIG. 1 inserted into a patient.

The cover 150 is preferably a polymer, such as polytetrafluoroethylene PTFE, that will allow an introducer device, such as a syringe needle (not shown), to be inserted through the cover 150 and removed from the cover, without fluid in the channel 120 leaking from the cover 150. Optionally, support struts 154 may extend across the channel 120 to provide support to the cover 150. The struts 154 may be constructed from a metal, a polymer, or some other suitable material. They may be separate pieces or interconnected by a framework (not shown) but positioned and spaced so as not to interfere with needle penetration but may be sufficiently close to provide needle guidance and support, and may be embedded within the material of the cover or be along the top or bottom surface thereof In use, the discharge port 116 is connected to the proximal end 202 of a catheter 200, such as is shown in FIG. 4. The catheter 200 is a single lumen catheter, such as the TESIO® catheter, manufactured by Medical Components, Inc. of Harleysville, Pa. The proximal end 202 of the catheter 200 includes a female connector 204 that is adapted to threadably connect to the threaded connector 134.

The catheter 200 is subcutaneously implanted within a patient's tissue "T" according to known methods. However, instead of the proximal end 204 of the catheter 200 exiting the patient as in conventional catheterization, the distal end 204 of the catheter 200 remains subcutaneous in the tissue.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A port for transmitting a fluid to a conduit, comprising:
   a narrow elongated body having:
      a proximal end;
      a distal end having a discharge port extending exterior from the body for connection to a conduit; and
      a first and second pair of substantially parallel planar side walls defining a single elongated channel extending between the proximal and distal ends, wherein the channel is in fluid communication with the exterior of the body through the discharge port; and
   a cover fixedly connected to the body and extending over the channel such that the channel is wholly contained within the body and the cover, and the cover is constructed from a polymer and is self-sealing to permit needle insertion and to seal upon needle withdrawal,
   wherein the body and the cover have inside surfaces defining the channel, wherein all surfaces bounding the channel are generally rounded and smooth and are free of sharp edges and corners.

2. The port according to claim 1, wherein the body is constructed from a metal.

3. The port according to claim 1, wherein the cover further comprises at least one support strut extending therethrough intermediate the proximal and distal ends.

4. The port according to claim 3, wherein the at least one support strut extends across the channel.

5. The port according to claim 3, wherein the at least one support strut is interconnected by a framework.

6. The port according to claim 3, wherein the at least one support strut is embedded within the cover.

7. The port according to claim 1, wherein the channel comprises a generally concave shape.

8. The port according to claim 1, wherein the cover comprises a generally convex shape with a concave bottom surface.

9. The port according to claim 1, wherein the body is adapted to be secured to a patient.

10. The port according to claim 1, wherein the elongated body has a constant width.

11. The port according to claim 1, wherein the elongated body has exterior surfaces that are continuous with an exterior surface of the cover.

12. An implantable port, consisting essentially of:
   an elongated body, comprising:
      a proximal end,
      a distal end; and
      a first and second pair of substantially parallel planar vertical side walls defining a single elongated channel extending between the proximal end and the distal end;
   a needle penetrable cover affixed to the elongated body having a generally convex exterior surface and a generally concave interior surface; and
   a discharge port deposited at the distal end of the elongated body, wherein the discharge port is in fluid communication with the channel,
   wherein the elongated body and the cover have interior surfaces defining the channel, wherein all surfaces bounding the channel are generally rounded and smooth and are free of sharp edges and corners.

13. The implantable port of claim 12, wherein the cover is supported by a at least one support strut extending across the channel.

* * * * *